(12) United States Patent
Bhattacharya et al.

(10) Patent No.: US 7,129,211 B2
(45) Date of Patent: Oct. 31, 2006

(54) ADIPOCYTE INSULIN ADPINSL WITH INSULIN A AND B CHAINS AND AN EFFECTIVE METHOD OF TREATING TYPE 2 DIABETES IN A SUBJECT USING ADIPOCYTE INSULIN

(75) Inventors: Samir Bhattacharya, Calcutta (IN); Sib Sankar Roy, Calcutta (IN); Subrata Dasgupta, Santiniketan (IN); Mohua Mukherjee, Calcutta (IN)

(73) Assignees: Council of Scientific and Industrial Research, New Delhi (IN); Department of Biotechnology Department of the Government of India, New Delhi (IN)

( * ) Notice: Subject to any disclaimer, the term of this patent is extended or adjusted under 35 U.S.C. 154(b) by 467 days.

(21) Appl. No.: 10/396,551

(22) Filed: Mar. 26, 2003

(65) Prior Publication Data

US 2004/0053816 A1 Mar. 18, 2004

Related U.S. Application Data

(60) Provisional application No. 60/367,212, filed on Mar. 26, 2002.

(51) Int. Cl.
*A61K 38/28* (2006.01)
*C07H 21/04* (2006.01)
*C07K 14/62* (2006.01)

(52) U.S. Cl. .................. 514/3; 530/303; 536/23.5; 435/69.4; 435/320.1; 435/325

(58) Field of Classification Search .................. None
See application file for complete search history.

(56) References Cited

OTHER PUBLICATIONS

Roy et al. A New Cell Secreting Insulin. Endocrinology, Apr. 2003, vol. 144, No. 4, pp. 1585-1593.*
Makower et al. Carp Insulin: Amino Acid Sequence, Biological Activity and Structural Properties. Eur J Biochem, 1982. vol. 122, pp. 339-345.*

* cited by examiner

*Primary Examiner*—Bruce R. Campell
*Assistant Examiner*—Marcela M Cordero Garcia
(74) *Attorney, Agent, or Firm*—Oliff & Berridge, PLC

(57) ABSTRACT

The present invention relates to an adipocyte Insulin adpInsl with Insulin A and B chains of SEQ ID Nos. 1 and 2, a effective method of treating type 2 diabetes in a subject using adipocyte insulin, said method comprising steps of administering the insulin to a diabetic intraperitoneally, an Insulin gene of SEQ ID No. 3, a process of isolating protein Insulin from the adipocytes of the Carp, said method comprising steps of reverse transcripting RNA of adipocytes to obtain cDNA, using oligonucleotide primers of SEQ ID Nos. 5 and 6 to identify AdpInsl gene from cDNA, and deducing amino acid sequence from cDNA to obtain protein Insulin, and an adipocyte of Catla Catla useful for producing the said Insulin.

Figure 1A:
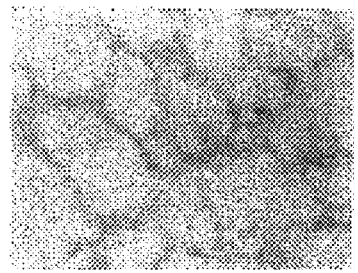

13 Claims, 12 Drawing Sheets
(7 of 12 Drawing Sheet(s) Filed in Color)

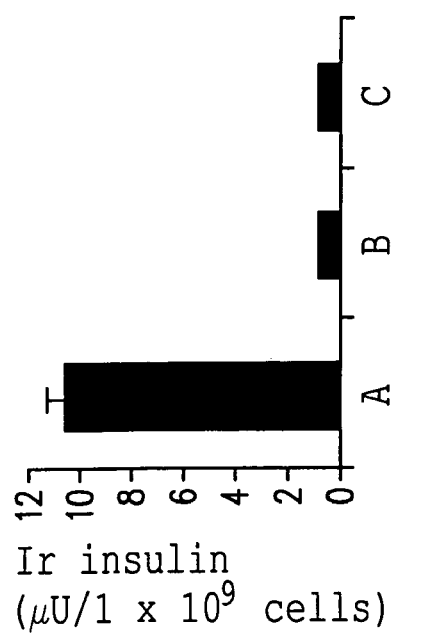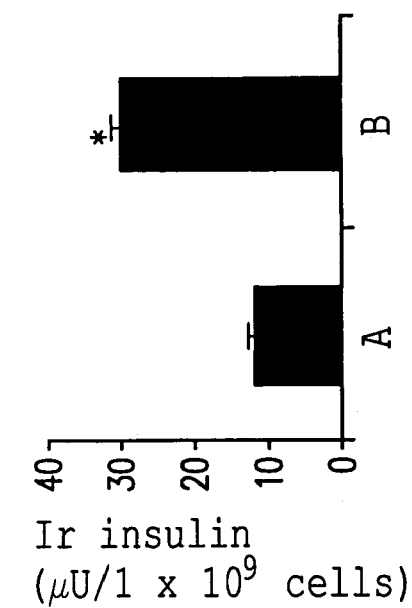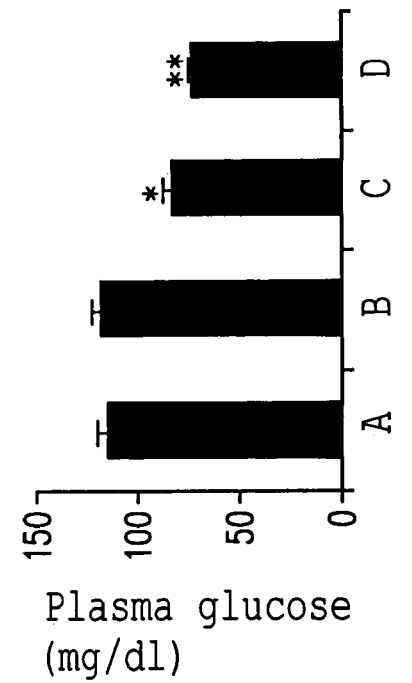
Fig. 2A
Fig. 2B
Fig. 2C

```
  1                                                  gtgacc
  7 atggcagtgtggctccaggctggtgctcttttgttcttgttggcc
    M  A  V  W  L  Q  A  G  A  L  L  F  L  L  A       SP
                        ↓
 52 gtctccagtgtgaacgctaacccaggggccccacagcatctatgt
    V  S  S  V  N  A  N  P  G  A  P  Q  H  L  C 97 ggatctcatctggtcgatgccctctacctggtctgtggtccaaca
    G  S  H  L  V  D  A  L  Y  L  V  C  G  P  T       B
                        ↓
142 ggattcttctacaaccccaagagagacgttgaccctcttatgggt
    G  F  F  Y  N  P  K  R  D  V  D  P  L  M  G 187 ttccttcctccaaaatctgcccaggaaactgaggtagctgacttt
    F  L  P  P  K  S  A  Q  E  T  E  V  A  D  F       C
                              ↓
232 gcatttaaagatcatgccgaggtgataaggaagagaggcattgtg
    A  F  K  D  H  A  E  V  I  R  K  R  G  I  V 277 gagcagtgttgccacaaaccctgcagtatctttgagctgcagaac
    E  Q  C  C  H  K  P  C  S  I  F  E  L  Q  N       A 322 tactgtaactaaagaacctgcacgtcttgtgacaactgccaatga
    Y  C  N  *

367 ctttcccctgtttgcacacaggtatctgccttatgctcttgtttg
395 tttcatagaaattaaaatttttcaatga
```

Fig. 7A

INSULIN A CHAIN:

```
              ↓↓                              ↓
     Human   GIVEQCC TSI CS LYQ LE NYCN
       Pig   GIVEQCC TSI CS LYQ LE NYCN
       Rat   GIVDQCC TSI CS LYQ LE NYCN
Zebra fish   GIVEQCC HKP CS IFE LQ NYCN
 Adipocyte   GIVEQCC HKP CS IFE LQ NYCN
              ↑  ↑↑   ↑
```

INSULIN B CHAIN:

```
                                        ↓↓
     Human   FVN QHLCGSHLV EALYLVCG ERGFFY TPKT
       Pig   FVN QHLCGSHLV EALYLVCG ERGFFY TPKA
       Rat   FVK QHLCGSHLV EALYLVCG ERGFFY TPKS
Zebra fish   PGTP QHLCGSHLV DALYLVCG PTGFFY NPK
 Adipocyte   PGAP QHLCGSHLV DALYLVCG PTGFFY NPK
                   ↑                    ↑↑
```

Fig. 7B

```
                1         10         20         30         40         50        59
Human IR    HLYPGEVC-PGMDIRNDLTRLHELEHCSVIEGHLQILLMFKTRPEDFRDLSPPKLDNITD
                 |+| ||+||||+  +|  ||||+||||+| |||+  ++ ||+|    |||| +||+
IGF-1R      -----EICGPGIDIRNDYQQLKRLEHCTVIEGYLHILLI--SKAEDYRSYRPPKLTVITE 60         70         80         90        100        110       119
Human IR    YLLLFRVYGLESLKDLPPNLTVIRGSRLFFHYALVIFEMVHLKELGLYNLMNITRGSVRI
            ||||||| |||||| ||||||||||||| +||+|||||||||  +||++||||| |||||++||
IGF-1R      YLLLPRVAGLRSLGDLPPNLTVIRGWKLFYNYALVIFEMTNLKDIGLYNLRNITRGAIRI 120        130        140        150        160        170       179
Human IR    EKNNELCYLATIDWSRILDSVEDNYIVLNKDDHEECGDICPGIAKGKIHCPATVINGQFV
            ||| +||||+|+||| |||+| +|||| ||   +||||+|||| + | | | || ++
IGF-1R      EKNADLCYLSTVDWSLILDAVSNNYIVGNKPP-KECGDLCPGTMEEKPHCEKTTINNEYN 180        190        200        210        220        230       239
Human IR    ERCWTHSHCQKVCPTICKSHGCTAEGLCCHSECLGHCSQPDDPTKCVACRNPYLDGRCVE
            ||||  +  |||+||+  |    ||    ||| ||||+|| ||+ |  |||||+++|  ||
IGF-1R      YRCWTTHRCQKMCPSTCGKRACTEHNECCHPECLGSCSAPDHDTACVACRHYYYAGVCVP 240        250        260        270        280        290       299
Human IR    TCPPPYYHFQDWRCVNFSPCQDLHCKCKNSRRQGCHQYVIHDNKCIPECPSGYTGMSSNL
            |||   | |+ ||||+  || ++   ++| +|  +|||+ +|+ ||||+     | |
IGF-1R      ACPPNTYRFEGWRCVDRDFCAHI-LSAESSDSEG---FVIHDGECMQECPSGFIRNGSQS 301        309        319        329        339        349       358
Human IR    L-CTPCLGPCPKVCHLLEGEKTIDSVTSAQELRGCTVIHGSLIINIRGGHNLAAELEANL
            + | || ||||||    +  |||||||||| |+|||+  |+|+||||  |||+|+|||   +
IGF-1R      MYCIPCEGPCPKVCEEEKKTKTIDSVTSAQDLQGCTIFKGHLLIHIRRGNNIASELENPH 359        369        379        389        399        409       418
Human IR    GLIEEISGYLKIRRSYALVSLSFFRKLRLIRGETLEIGNYSFYALDHQHLRQLWDWSKHN
            ||||  ++||+|||   |+||||||||| +  |||| ||      |||||| ||||||+||||+      |
IGF-1R      GLIEVVTGYVKIRHSHALVSLSFLKHLRLILGEEQLEGNYSFYVLDHQNLQQLWDWDHRN 419        429        439        449        459       471
Human IR    LTITQGKLPPHYNPKLCLSEIHMMEEVSGTKGRQERNDIALKTHGDQASCENE
            |||  ||++|  +|||||+|||++||||+|+|||||| + ||  +  ||++||||  |
IGF-1R      LTIKAGKMYFAFNPKLCVSEIYRMEEVTGTKGRQSKGDINTRNHGERASCEKE
```

Fig.-8

SEQUENCE LISTING

```
<160> NUMBER OF SEQ ID NOS: 16

<210> SEQ ID NO 1
<211> LENGTH: 21
<212> TYPE: PRT
<213> ORGANISM: Catla catla

<400> SEQUENCE: 1

Gly Ile Val Glu Gln Cys Cys His Lys Pro Cys Ser Ile Phe Glu Leu
1               5                   10                  15

Gln Asn Tyr Cys Asn
            20

<210> SEQ ID NO 2
<211> LENGTH: 30
<212> TYPE: PRT
<213> ORGANISM: Catla catla

<400> SEQUENCE: 2

Pro Gly Ala Pro Gln His Leu Cys Gly Ser His Leu Val Asp Ala Leu
1               5                   10                  15

Tyr Leu Val Cys Gly Pro Thr Gly Phe Phe Tyr Asn Pro Lys
            20                  25                  30

<210> SEQ ID NO 3
<211> LENGTH: 439
<212> TYPE: DNA
<213> ORGANISM: Catla catla
<220> FEATURE:
<221> NAME/KEY: CDS
<222> LOCATION: (7)..(330)

<400> SEQUENCE: 3 gtgacc atg gca gtg tgg ctc cag gct ggt gct ctt ttg ttc ttg ttg      48
       Met Ala Val Trp Leu Gln Ala Gly Ala Leu Leu Phe Leu Leu
       1               5                   10
```

```
                                                         -continued
gcc gtc tcc agt gtg aac gct aac cca ggg gcc cca cag cat cta tgt      96
Ala Val Ser Ser Val Asn Ala Asn Pro Gly Ala Pro Gln His Leu Cys
 15              20                  25                  30 gga tct cat ctg gtc gat gcc ctc tac ctg gtc tgt ggt cca aca gga     144
Gly Ser His Leu Val Asp Ala Leu Tyr Leu Val Cys Gly Pro Thr Gly
             35                  40                  45 ttc ttc tac aac ccc aag aga gac gtt gac cct ctt atg ggt ttc ctt     192
Phe Phe Tyr Asn Pro Lys Arg Asp Val Asp Pro Leu Met Gly Phe Leu
             50                  55                  60 cct cca aaa tct gcc cag gaa act gag gta gct gac ttt gca ttt aaa     240
Pro Pro Lys Ser Ala Gln Glu Thr Glu Val Ala Asp Phe Ala Phe Lys
             65                  70                  75 gat cat gcc gag gtg ata agg aag aga ggc att gtg gag cag tgt tgc     288
Asp His Ala Glu Val Ile Arg Lys Arg Gly Ile Val Glu Gln Cys Cys
 80              85                  90 cac aaa ccc tgc agt atc ttt gag ctg cag aac tac tgt aac             330
His Lys Pro Cys Ser Ile Phe Glu Leu Gln Asn Tyr Cys Asn
 95              100                 105 taaagaacct gcacgtcttg tgacaactgc caatgacttt ccctgtttg cacacaggta    390 tctgccttat gctcttgttt gtttcataga aattaaaatt tttcaatga              439

<210> SEQ ID NO 4
<211> LENGTH: 108
<212> TYPE: PRT
<213> ORGANISM: Catla catla

<400> SEQUENCE: 4

Met Ala Val Trp Leu Gln Ala Gly Ala Leu Leu Phe Leu Leu Ala Val
 1               5                   10                  15

Ser Ser Val Asn Ala Asn Pro Gly Ala Pro Gln His Leu Cys Gly Ser
             20                  25                  30

His Leu Val Asp Ala Leu Tyr Leu Val Cys Gly Pro Thr Gly Phe Phe
         35                  40                  45

Tyr Asn Pro Lys Arg Asp Val Asp Pro Leu Met Gly Phe Leu Pro Pro
     50                  55                  60

Lys Ser Ala Gln Glu Thr Glu Val Ala Asp Phe Ala Phe Lys Asp His
 65                  70                  75                  80

Ala Glu Val Ile Arg Lys Arg Gly Ile Val Glu Gln Cys Cys His Lys
                 85                  90                  95

Pro Cys Ser Ile Phe Glu Leu Gln Asn Tyr Cys Asn
             100                 105

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide forward primer for identifying
      AdpIns1 gene

<400> SEQUENCE: 5
gggaattcca gcacctgtgt ggatc                                          25

<210> SEQ ID NO 6
<211> LENGTH: 22
<212> TYPE: DNA
<213> ORGANISM: Artificial Sequence
<220> FEATURE:
<223> OTHER INFORMATION: Reverse oligonucleotide primer for identifying
      AdpIns1 gene
```

-continued

```
<400> SEQUENCE: 6
gggaattcgt gaccatggca gt                                              22

<210> SEQ ID NO 7
<211> LENGTH: 21
<212> TYPE: PRT
<213> ORGANISM: Homo sapiens

<400> SEQUENCE: 7

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 8
<211> LENGTH: 30
<212> TYPE: PRT
<213> ORGANISM: Homo sapiens

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 9
<211> LENGTH: 21
<212> TYPE: PRT
<213> ORGANISM: Sus scrofa

<400> SEQUENCE: 9

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 10
<211> LENGTH: 30
<212> TYPE: PRT
<213> ORGANISM: Sus scrofa

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

<210> SEQ ID NO 11
<211> LENGTH: 21
<212> TYPE: PRT
<213> ORGANISM: Rattus rattus

<400> SEQUENCE: 11

Gly Ile Val Asp Gln Cys Cys Thr Ser Ile Cys Ser Leu Tyr Gln Leu
1               5                   10                  15

Glu Asn Tyr Cys Asn
            20

<210> SEQ ID NO 12
<211> LENGTH: 30
<212> TYPE: PRT
<213> ORGANISM: Rattus rattus
```

```
<400> SEQUENCE: 12

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Lys Ser
                20                  25                  30

<210> SEQ ID NO 13
<211> LENGTH: 21
<212> TYPE: PRT
<213> ORGANISM: Brachydanio rerio

<400> SEQUENCE: 13

Gly Ile Val Glu Gln Cys Cys His Lys Pro Cys Ser Ile Phe Glu Leu
1               5                   10                  15

Gln Asn Tyr Cys Asn
                20

<210> SEQ ID NO 14
<211> LENGTH: 30
<212> TYPE: PRT
<213> ORGANISM: Brachydanio rerio

<400> SEQUENCE: 14

Pro Gly Thr Pro Gln His Leu Cys Gly Ser His Leu Val Asp Ala Leu
1               5                   10                  15

Tyr Leu Val Cys Gly Pro Thr Gly Phe Phe Tyr Asn Pro Lys
                20                  25                  30

<210> SEQ ID NO 15
<211> LENGTH: 25
<212> TYPE: DNA
<213> ORGANISM: Artificial Sequence
<220> FEATURE:
<223> OTHER INFORMATION: oligo (dT) primer

<400> SEQUENCE: 15 ggaagcttttt tttttttttt ttttt                                    25

<210> SEQ ID NO 16
<211> LENGTH: 8
<212> TYPE: PRT
<213> ORGANISM: Homo sapiens

<400> SEQUENCE: 16

Gly Ile Val Glu Gln Cys Cys Thr
1               5
```

ADIPOCYTE INSULIN ADPINSL WITH INSULIN A AND B CHAINS AND AN EFFECTIVE METHOD OF TREATING TYPE 2 DIABETES IN A SUBJECT USING ADIPOCYTE INSULIN

FIELD OF THE PRESENT INVENTION

The present invention relates to an adipocyte Insulin adpInsl with Insulin A and B chains of SEQ ID Nos. 1 and 2, a effective method of treating type 2 diabetes in a subject using adipocyte insulin, said method comprising steps of administering the insulin to a diabetic intraperitoneally, an Insulin gene of SEQ ID No. 3, a process of isolating protein Insulin from the adipocytes of the Carp, said method comprising steps of reverse transcripting RNA of adipocytes to obtain cDNA, using oligonucleotide primers of SEQ ID Nos. 5 and 6 to identify AdpInsl gene from cDNA, and deducing amino acid sequence from cDNA to obtain protein Insulin, and an adipocyte of Catla Catla useful for producing the said Insulin.

BACKGROUND AND PRIOR ART REFERENCE OF THE PRESENT INVENTION

Insulin gene expression and secretion of insulin protein in all animals including human being is still known to be pancreatic p-cell specific. Search for an alternative insulin besides pancreatic P-cell has not yet been successful. Insulin like material was detected in bacteria, *E. coli* (1), immunoreactive and bioactive insulin was found in insects and annelids (2) and extra pancreatic distribution of insulin was reported in rat and human (3–16). But insulin gene expression and protein secretion from these sources is not known.

OBJECTS OF THE PRESENT INVENTION

The main object of the present invention is to develop an adipocyte Insulin adpInsl with Insulin A and B chains of SEQ ID Nos. 1 and 2.

Another main object of the present invention is to develop an effective method of treating type 2 diabetes in a subject using adipocyte insulin.

Yet another object of the present invention is an Insulin gene of SEQ ID No. 3.

Still another object of the present invention is to develop a process of isolating protein Insulin from the adipocytes of the Carp.

Still another object of the present invention is to develop an adipocyte of Catla Catla useful for producing Insulin.

SUMMARY OF THE PRESENT INVENTION

The present invention relates to an adipocyte Insulin adpInsl with Insulin A and B chains of SEQ ID Nos. 1 and 2, a effective method of treating type 2 diabetes in a subject using adipocyte insulin, said method comprising steps of administering the insulin to a diabetic intraperitoneally, an Insulin gene of SEQ ID No. 3, a process of isolating protein Insulin from the adipocytes of the Carp, said method comprising steps of reverse transcripting RNA of adipocytes to obtain cDNA, using oligonucleotide primers of SEQ ID Nos. 5 and 6 to identify AdpInsl gene from cDNA, and deducing amino acid sequence from cDNA to obtain protein Insulin, and an adipocyte of Catla Catla useful for producing the said Insulin.

DETAILED DESCRIPTION OF THE PRESENT INVENTION

The present invention relates to an adipocyte Insulin adpInsl with Insulin A and B chains of SEQ ID Nos. 1 and 2, a effective method of treating type 2 diabetes in a subject using adipocyte insulin, said method comprising steps of administering the insulin to a diabetic intraperitoneally, an Insulin gene of SEQ ID No. 3, a process of isolating protein Insulin from the adipocytes of the Carp, said method comprising steps of reverse transcripting RNA of adipocytes to obtain cDNA, using oligonucleotide primers of SEQ ID Nos. 5 and 6 to identify AdpInsl gene from cDNA, and deducing amino acid sequence from cDNA to obtain protein Insulin, and an adipocyte of Catla Catla useful for producing the said Insulin.

In an embodiment of the present invention, wherein an adipocyte Insulin adpInsl with Insulin A and B chains of SEQ ID Nos. 1 and 2.

In yet another embodiment of the present invention, wherein the SEQ ID no. 1 is of length 21 amino acids.

In still another embodiment of the present invention, wherein the SEQ ID No. 2 is of length 30 amino acids.

In still another embodiment of the present invention, wherein the insulin shows amino acid residue Histidine at position eight of Insulin A chain.

In still another embodiment of the present invention, wherein the insulin shows 70% homology with human insulin.

In still another embodiment of the present invention, wherein the insulin shows segments A1–A4, A19, B12, and B24–B26 as receptor binding segments.

In still another embodiment of the present invention, wherein the binding regions of insulin is 100% identical to the corresponding regions of human insulin.

In still another embodiment of the present invention, wherein an effective method of treating type 2 diabetes in a subject using adipocyte insulin, said method comprising steps of administering the insulin to a diabetic intraperitoneally.

In still another embodiment of the present invention, wherein the insulin is of concentration ranging between 15 to 20 micrograms per 100 grams body weight. In still another embodiment of the present invention, wherein an Insulin gene of SEQ ID No. 3.

In still another embodiment of the present invention, wherein a process of isolating protein Insulin from the adipocytes of the Carp, said method comprising steps of:
  reverse transcripting RNA of adipocytes to obtain cDNA,
  using oligonucleotide primers of SEQ ID Nos. 5 and 6 to identify AdpInsl gene from cDNA,
  deducing amino acid sequence from cDNA to obtain protein Insulin.

In still another embodiment of the present invention, wherein the primer of SEQ ID No. 45 along with oligo (dT) primer produces DNA fragment of 375 bp.

In still another embodiment of the present invention, wherein the primer of SEQ ID No. 6 along with oligo (dT) primer produces DNA fragment of 425 bp.

In still another embodiment of the present invention, wherein an adipocite of Catla Catla useful for producing Insulin of claim 1.

Herein the Applicants describe the invention that carp adipocyte is an exceptional cell where insulin gene is expressed and protein is secreted as inmunoreactive and biologically active insulin. Adipocyte insulin gene has been cloned, amino acid sequence deduced and peptide structure compared with that of p-cell insulin. Three-dimensional structure of AdpInsl has been modeled to explain the results with the novel AdpInsl.

In an embodiment of the present invention amino acid sequence of AdpInsl A and B chain was deduced.

In an embodiment of the present invention the AdpInsl is functionally more active than porcine insulin in rat.

In yet another embodiment of the present invention AdpInsl stimulates glucose uptake by adipocyte more actively than porcine insulin. In still another embodiment of the present invention AdpInsl has His/8, a favorable substitute against unfavorable Thr/8 in human and porcine insulin, which explains the reason for greater biological activity.

In still another embodiment of the present invention AdpInsl acts on rat receptor, which is 96% identical with that of human, 100% identical in potential binding region, with higher efficiency than porcine insulin.

BRIEF DESCRIPTION OF THE ACCOMPANYING DRAWINGS

The patent or application file contains at least one drawing executed in color. Copies of this patent or patent application publication with color drawings will be provided by the office upon request and payment of the necessary fee.

Figure 1B:
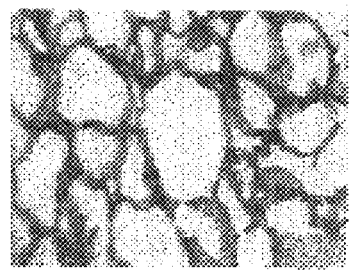

FIG. 1. Immunocytochemtstry of adipocyte showing the presence of insulin in control (a) and experimental (b) set. Paraffin embedded fat tissue was incubated with (b) or without (a, control) porcine insulin antibody (20 µg/ml) following 15 min incubation with 0.6% HaOs (v/v) in 80% methanol and then 45 min incubation with rabbit anti-guineapig Ig-HRP (diluted 1:100, v/v in 10% PBS). The reaction was developed using freshly prepared solution of 0.05% (w/v) DAB and 0.03% $H_2O_2$ in PBS FIG. 2. Immunoreactive and bioactive insulin from carp adipocytes. Adipocyte, liver and kidney cells were isolated and incubated in vitro in the manner already described in the experimental procedures, (a) Medium was collected on termination of incubation of adipocyte (A), liver (B) and kidney (C) cells and subjected to insulin RIA. Each value is the mean±SEM of 10 observations, (b) Rats were injected with 50 µg protein from adipocyte extract (C) or 20 ug protein from the incubation medium of adipocyte (D) or only medium (B) or without any injection (A). Blood was collected at 6 hr and glucose content was determined. Each value is the mean±SEM of 6 independent determinations. *$p<0.05$,**$p<0.01$ as compared with A and B (c) Secretion of insulin from adipocytes into the medium (5.5 mM glucose) (A.), effect of additional of 50 mM glucose into the medium (B). Each value is the mean±SEM of 5 observations. *$p<0.01$ in comparison to control.

FIG. 3. (a)–(c) Expression of adipocyte specific, markers (of 10 Og of RNA from adipocytes) was loaded and probed with radio labeled probe for flotiffin (Gift of Dr. Perry Bickel). (b) 10 Og, 20 Og, 30 Og of total protein (adipocyte cell extract) was run on SDS-PAGE (Jane 1, 2 and 3 respectively) with molecular size marker (lane 5) and transferred onto PVDF membrane and probed with anti-GLUT4 antibody, (c) 25 Og of total protein (adipocyte cell extract) was loaded on SDS-PAGE (lane 2) and transferred onto PVDF membrane and probed with anti-GLUT4 antibody. Molecular size marker was loaded on lane 1. FIG. 3. (d) High magnification confocal fluorescence microscopy of adipocytes. Confocal microscopy of the adipocytes was performed on a layer of cells adhered on poly-L lysine coated slides. The fixed, permeabilized and blocked cells were double labeled with Leptin rabbit polyclonal and Insulin mouse monoclonal antibodies. The secondary antibodies used were FITC and TRTTC conjugated anti-rabbit and anti-mouse secondary antibodies. (A) Differential interference contrast (DIG) showing carp adipocytes, (B) Carp adipocytes showing the expression of leptin, (C) Carp adipocytes showing the expression of insulins (D) Co-localization of leptin and insulin, and (E) Rat adipocyte stained with anti-human insulin mouse monoclonal primary antibody and TRTTC conjugated goat anti-mouse secondary antibody.

Figure 4:
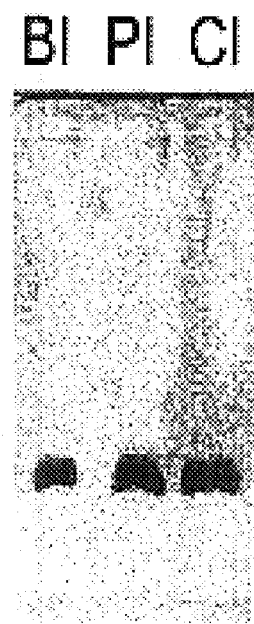

FIG. 4. Co-migration of purified carp fat cell insulin (CI) with bovine (BI) and porcine insulin (PI). 5 ug of each insulin was subjected to 5–15% gradient SDS-PAGE followed by coomassie blue staining.

FIG. 5. Determination of biological activity of purified adipocyte insulin on streptozotocin induced diabetic rat. (a) The male Sprague Dawley rats of 100–150 g weight were selected for streptozotocin (STZ) treatment. 55 nig/Kg STZ was intraperitoneally injected into the rat, those animals exhibited 250–320 mg % glucose level on third week of injection were taken for experiments. (A) STZ untreated rats, only vehicle (0.9% saline) injected (n-6), (B) STZ rat, vehicle injected (n-6), (C) STZ rat injected with AdpInsl 10 µg/100 g body wt of rat (n-6). (D) STZ rat injected with 10 ug/100 g body wt of rat (n=6J porcine insulin. Each value is ±SEM of 6 observations. $p<0.001$ when C is compared with B,**$p<0.05$ when C is compared with D.

(b) Effect of AdpInsl and porcine insulin (PI) on glucose uptake by carp adipocytes. Adipocytes $1\times10^5$ cells/incubation, suspended in MEM containing 1% fetal calf serum and preincubated for 2 hours in the absence of insulin, after addition of D-$^{14}$C-glucose uptake was determined by the procedure described under the "Experimental procedures". *$p<0.05$ when AdpInsl is compared with porcine insulin.

FIG. 6. Expression of Insulin gene in adipocytes. (a) 10 Og each of total carp adipocyte RNA (lane 1 and 2) and carp kidney (lane 3, were electrophoresed and transferred onto Nytran membrane. It was then probed with rat insulin cDNA (lane 1) and zebrafish insulin cDNA (lane 2 and 3).

(b) 10 Og each of total RNA from adipocytes of rat (lane 1], guineapig (lane 2), hamster (lane 3) and carp (lane 4) were electrophoresed and transferred onto Nytran membrane. It was then probed with zebrafish insulin cDNA.

FIG. 7. (a) Nucleotide and the deduced amino acid sequences of the preproinsulin gene of carp (SEQ ID NOs: 3 and 4, respectively) showing signal peptide (SP) (1–22 aa), B (23–52 aa), C (53–87 aa) and A (88–108 aa) chain. The UTR sequence also has been shown. The lower case letters represent the nucleic acid sequence, while the amino acids are represented by the upper case letters. The start codon is underlined and the stop codon is indicated by an asterisk. The probable cleavage sites between the signal peptide and B, between B and C and between the C and A are represented by vertical arrows. FIG. 7. (b) Comparison of the predicted amino acid sequences of insulin A and B chains of human (SEQ ID NOs: 7 and 8, respectively), pig (SEQ ID NOs: 9 and 10, respectively), rat (SEQ ID NOs: 11 and 12, respectively), zebrafish (SEQ ID NOs: 13 and 14, respectively) and adipocyte of Indian carp (SEQ ID NOs: 1 and 2, respectively). Their positional homology was examined. The box represents the homologous domains whereas the letter in bold in the box shows the nonidentical aa. Mutations of the residues at the positions designated by the arrows that point down are most disruptive mutations (to Ala) in terms of receptor binding of human insulin (12) in (a). The position of other amino acids which are also known to be involved in the receptor binding are designated by arrows pointing up (16) in (b).

FIG. 8. Sequence alignment of the human insulin receptor (Human IR) and type-1 insulin like growth factor receptor (IGF-1R). Vertical lines indicate identical aa, (+) signs indicate conservative mutations and blanks indicate non-conservative mutations. (−) sign on the human IR sequence indicate the locations of aa deletions and sign on the IGF-1R sequence indicate aa insertions. Numbers on the top line are the serial aa numbers of the human IR as used for the identification of aa in the text.

Figure 9:
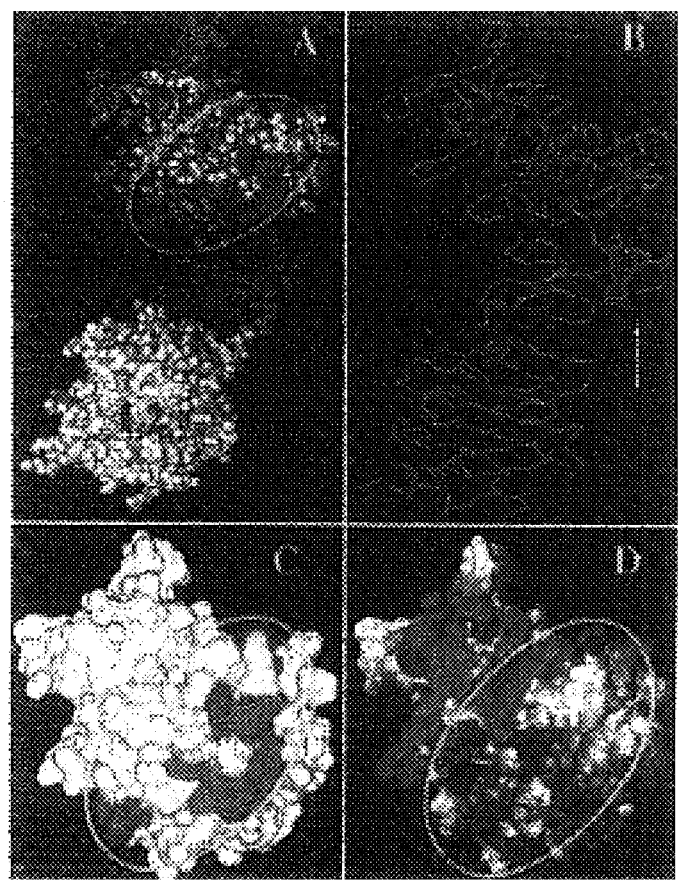

FIG. 9. (A) shows the space-filling representation LI. Cys-Rich and L2 domains of the modeled human IR based the x-ray structure of IGR-1R. The region of LI domain marked with the yellow band has been identified to harbor the ligand-binding complementary site on the basis of alanine scanning mutagenesis (shown as a magnified version in panel C). Amino acids Arg-14, Asn-15 and Phe-64 mutations of which to alanine cause about 300 fold reduction in the ligand-binding affinity are colored in red; lie-13, Gin-34, Leu-36 and Phe-3*Mvhich cause 10–100 fold reduction in affinity are colored pink and Asp-12, Met-38, Glu-44, Tyr-66, Phe-89, Asn-90 and Tyr-91 which cause 3–9 fold reduction in the binding affinity are colored light blue. (B) shows the structural superposition of modeled human IR (red) with the corresponding x-ray structure of IGR-1R (green). (C) shows the surface of the LI domain of the modeled human insulin receptor oriented to bring the potential ligand-binding area to the front (inside the yellow band); surface colors are the same as described in panel A. (D) shows the same surface as that in panel C but colored according to the electrostatic potential at the of the surface. Blue color depicts the positively charged basic regions; red color shows the negatively charged acidic regions and white color is for the neutral hydrophobic regions and the regions of intermediate colors arise due to the net result of mixed electrostatic potentials.

Figure 10:
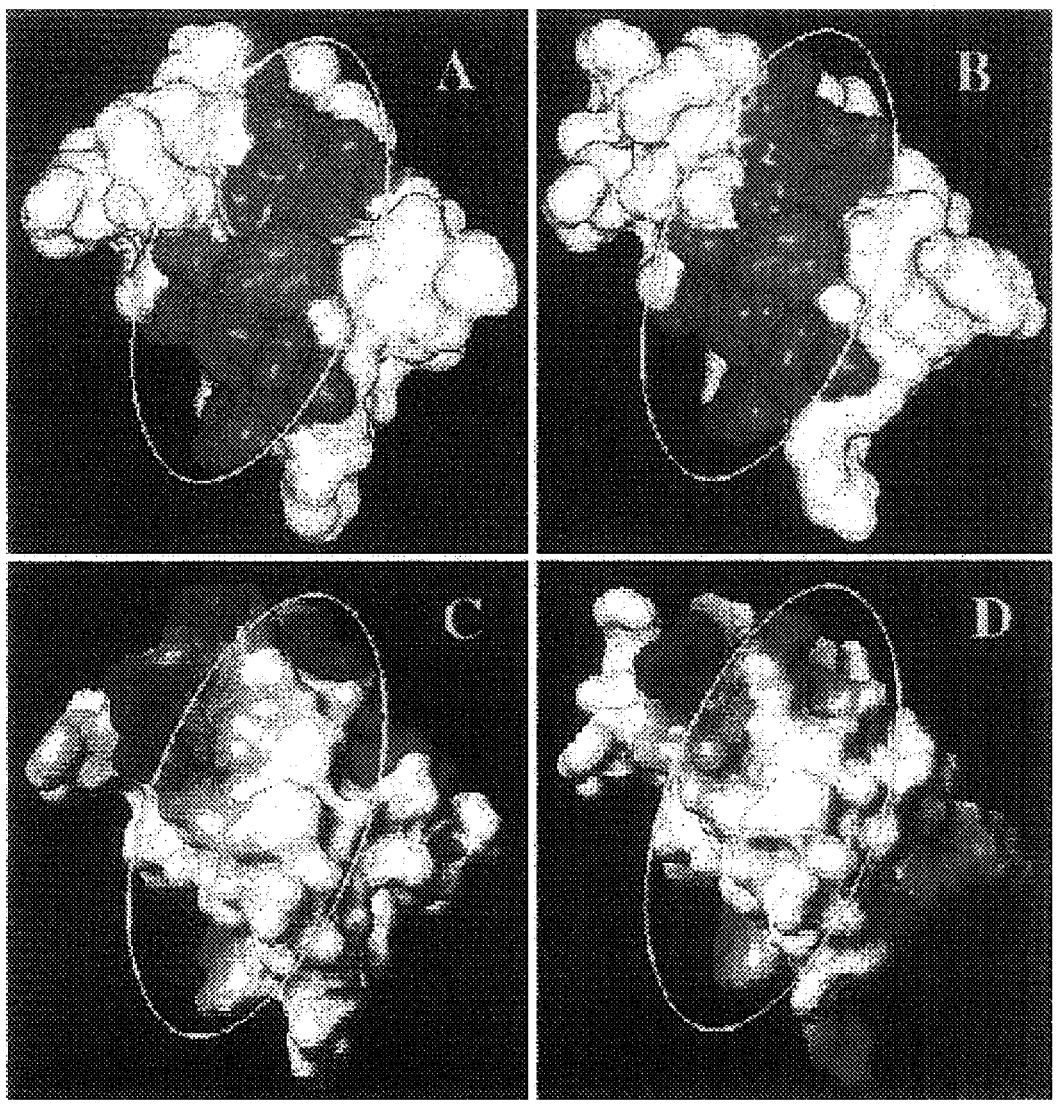

FIG. 10. (A) shows the connolly surface of the modeled monomer of AdpInsl calculated using Insight!!. Residues Gly-B23, Phe-B24, Ile-A2, Val-A3 and Tyr-A19 which are strongly implicated in receptor-binding as evidenced by different experimental techniques are colored in red and some other amino acids, Phe-B25, Tyr-B26, His-BlO, Gly-Al, Glu-A3, Gln-A4, and His-A8, which are known to affect the receptor binding to some extent have been colored pink. The structure was oriented in such a way that the highly potential receptor-binding surface is fully exposed (within the yellow band). (B) shows the connolly surface of the reference human monomer in the same orientation with the same color convention (only exception is that the aa at A8 position is Thr instead of His in the human insulin). (C) shows the same surface as that in panel C but coloured according to the electrostatic potential at the of the surface and calculated using MOLMOL. Blue color depicts the positively charged basic regions; red color shows the negatively charged acidic regions and white colour is for the neutral hydrophobic regions and the regions of intermediate colors arise due to the net result of mixed electrostatic potentials. (D) shows the equivalent electrostatic potential surface of the human insulin monomer in the same orientation.

EXPERIMENTAL PROCEDURES

Adipocyte culture—Cells from fat tissue, liver and kidney from the carp Catla catla were isolated and incubated in the following manner. Fat tissue around the small intestine of carp were collected in a petridish, minced with the help of a fine scissors, then transferred to a 50 ml beaker containing minimum essential medium (MEM without calcium, salinity was adjusted to 0.6%) containing collagenase type 11 (0.6 mg/ml), 3% BSA fraction V fatty acid free. This was incubated at 30° C. for 1 h with occasional stirring. On termination of the incubation, the beaker was placed at 42*C in a water bath for 10 min followed by a rapid filtration through tightly meshed nylon cloth. Cells">were washed with MEM-EDTA and viability of the cells was determined by the exclusion of the Trypan blue (0.1%) dye and no mortality was observed till 10 hours in the incubation medium. Cells were incubated with Ca2+free MEM (glucose 5.5 mM) containing 25 mM HEPES, 100 IU/ml Penicillin, 100 ug/ml Streptomycin and 1 mM' PMSF (pH 7.4). Adipocytes were diluted in this medium and incubated in 60 mm sterile tissue culture dish (1×10* cells/ml) for 4 h in an atmosphere of air. To prepare liver and kidney cells, liver and kidney tissue from carp were cut into small pieces and i transferred to 30 ml plastic centrifuge tube, which contained MEM (salinity adjusted 0,6%). The liver and kidney fragments (1 g/10 ml of medium) were incubated i for min at 30° C. with gentle shaking (40 cycles/min) in a water bath under constant' gassing with a mixture of 95% $O_{2-5}$% "CO?. This process was repeated by changing the medium so that liver and kidney fragments were properly washed and then transferred to MEM containing 0.5% collagenase. The 'tissues were incubated for 60 min and' aliquots examined for the presence of isolated liver and kidney cells. Under this; condition about 75% of liver tissue and 60% of kidney tissue became softened and cells were dispersed by collagenase. The soft tissue of liver and kidney remained in the test tube and the aliquot containing the cell suspension was collected by Pasteur pipette and transferred to plastic tube, centrifuged at 250 g. The pellet containing cells were re-washed in MEM (without collagenase). The cell suspensions were examined for morphological integrity and viability by the exclusion of 0.1% Trypan blue and in both the cases viability was between 80–90%. Isolated liver and kidney cells were distributed•among 60 mm sterile tissue culture dish (1×10s cells/ml) and incubated similarly as described above. On termination of incubation at 4 h, aliquots from the medium of different cell incubations were subjected to insulin RIA developed with anti-porcine insulin antibody.

Northern blot Analysis-RNA was isolated by Tri-Pure RNA extraction kit following the manufacturer's instructions. 10 pg of total RNA was loaded on each lane of a 1.5% formaldehyde-agarose gel, electrophoresed, and transferred to a nylon membrane by capillary suction method. The membranes were hybridized by the following probes: 349 bp SomH 1 digested fragment of rat insulin cDNA clone present in pGEM-T vector; 450 bp EcoRl-Hind III fragment of zebrafish preproinsulin cDNA clone present in pBluescript vector and 1.3 kb BomHl-Not 1 fragment of rat flotillin cDNA clone present in pZero-2 vector. Prehybridization was allowed for two hours in the buffer containing 6×SSC with 50% formamide, 1×Denhardt's solution and 0.5% SDS at 42° C. Hybridization was carried out in the same condition with the [alpha-$p^{32}$]dATP-labelled rat and zebra fish preproinsulin cDNA fragments for 18 h. The membrane was washed for 90 min at 65° C. in 2×SSC containing 0.1% SDS with subsequent three changes of buffer. The hybridized membrane was exposed to X-ray film and kept at −80° C. for 3 days. RNA molecular size markers (0.28–6.5 kb} used were purchased. Random labeling The digestion of DNA, agarose gel electrophoresis, random labeling of DNA and Northern hybridization was performed as described by Sambrook et al (18).

Western Blot Analysis—The isolated cells were homogenized in homogenizing buffer (150 mM NaCl, 500 mM Tris, 10 mM EDTA) supplemented with protease inhibitors (1ug/ml aprotinin, 1ug/ml pepstatin, 1ug/ml leupeptin, 1mM PMSF, 1 microg/ml trypsin inhibitor) and 1% Triton X-100. It was then centrifuged at 5,000 rpm for 10 min at 4° C. The supernatant was collected and an aliquot was taken for protein assay. Protein was quantified by the method described by Lowry et al (19) and then resolved on a 10% SDS-polyacrylamide gel and transferred to Immobilon-P membranes. Membrane was incubated with 5% blocking solution (Tris Buffered Saline [TBS] containing 0.1% Tween-20, 5% non-fat dried milk) for 1 hr, washed twice with TBST (TBS containing 0.1% Tween-20) and then incubated for 16 h with rabbit anti-GLUT4 (dilution 1:1000 in 5% blocking solution) or rabbit anti-PPARy (dilution 1:2000 in 5% blocking solution) antibody. Immunoreactive bands were visualized by reacting alkaline phosphatase-labeled secondary goat ant-rabbit antisera at 1:2000 dilution with the substrate NBT/BCIP (18)

Confocal microscopy—To determines the localization of insulin and leptin in the carp and rat adipocyte, cells were adhered on polyly sine-coated slide. Thereafter cells were fixed with 4% paraformaldehyde (PF) for 20 minutes at 4° C., permeabilized with permeabilization buffer (PB) containing Dulbecco's PBS without $Ca^{**}$ and $Mg^{*+}$, 1% heat inactivated PCS, 0.1% sodium azide and 0.1% Saponin, pH −7.4–7.6 and blocked with 2% goat serum containing 0.1% sodium azide and 0.1% Saponin. The cells were double-labeled with Leptin rabbit polyclonal and insulin mouse monoclonal antibodies. Cells were again washed with PB and incubated with FITC and TRITC conjugated goat anti-rabbit and anti-mouse secondary antibodies respectively. After washing the cells with PB with and without saponin, PBS containing 1% PF without saponin was added. The cells were finally mounted in 90% glycerol. For a negative control, the cells were fixed and immunofluorescence were conducted, but without any primary antibody, using only secondary antibody. Fluorescence was examined with a Leica TCS-SP (UV) 4-channel confocal laser scanning 'microscope. The cell monolayer was optically sectioned every 0.5 urn. Image resolution using a Leica 63× and/or 100× Neofluor objective and Leica TCS-SP software was 512-* 512 pixels.

Purification of carp fat cell insulin-Fat cells were lysed by sonication in ethanol:0.7M HCl (3:1, v/v) under ice and centrifuged at 5000 g for 10 min at 4° C. The pH of the supernatant was adjusted to 3.0 with concentrated ammonium solution and extracted with 4v of diethyl ether for 20 h at 4° C. The precipitate was washed with acetone followed by ether and allowed to air dry, this was then extracted with 1M acetic acid and centrifuged—The supernatant was re-extracted with chilled acetone and subjected to petroleum benzene extraction. The resultant precipitate was dried and extracted with chilled acetic acid (1M). The extracted material was gel filtered through Sephadex G-50 and insulin immunoreactive peak was lyophilized. This was further purified by FPLC reverse phase Pep-RFC column equilibrated with 0.1% (v/v) trifluroacetic acid/water. The fractions were eluted using acetonitrile linear gradients and amount of protein under each peak was measured according to the method of Lowry et al (19). Insulin immunoreactivity peak was pooled, lyophilized and subjected to 5–15% gradient SDS-PAGE (20}.

Insulin injection-Adipocyte IR-insulin (20 ug per 100 gm body weight) from incubation medium or 10 ug AdpInsl or porcine insulin was intraperitoneally injected into the male Sprague Dawley rats weighing between 100–150 g. After 6 hrs of injection blood was collected by retroorbital puncture using capillary tube, centrifuged to collect plasma and glucose content was determined by glucose-glucose oxidase method.

Determination of insulin activity in vitro—Freshly prepared adipocytes were suspended in the MEM and after 2 h 1.0 microCi of D-($^{14}$C) glucose (final concentration 25 uM| containing was added to the adipocyte incubation. 25 ng/ml of AdpInsl or porcine insulin was added to the incubation and uptake of glucose was measured by following a previously described method (21). Initial rates of glucose uptake was determined from the incubation of adipocyte without insulin. The reaction was stopped at 3 min by washing the cells three times with ice cold MEM in the presence of 0.3 mM phloretin to correct the glucose uptake data from simple diffusion and nonspecific trapping of radioactivity.

RT-PCR, Subcloning and Sequencing-Insulin gene fragments were isolated from carp fat cell RNA using reverse transcription coupled polymerase chain reaction (RT-PCR). First-strand cDNA synthesis was carried out with 10 ug of total RNA using Superscript II RT (GIBCO-BRL) enzyme. Oligo (dT) primer (5' GGAAGCTTTTTT-TTTTTTTTTTTTT 3' (SEQ ID NO: 15)), 10 uM dithiothreitol (DTT), 0.5 mM of each deoxynucleoside 5' triphosphate (dNTP), and the buffer supplied with enzyme (containing 50 mM Tris-HCl, pH 8.3, 75 mM KC1, 3 mM $MgCl_2$) were added to the RT reaction mixture (final volume 20 ul), and incubated at 42° C. for 1 hr. A 100 ul PCR reaction volume was made by adding 2.5 units of Taq DNA polymerase (GIBCO-BRL), to a PCR mixture containing 1 X reaction buffer (50 mM KC1, 10 mM Tris-HCl, pH 8.3, 0.1% Triton X100 and 2.5 mM $MgCl_2$), and 200 uM each dNTPs, 4 uM of each primers (sense and antisense) and 5 ul aliquot from RT reaction mixture. The sense primers (SB1–5' GGGAATTCCAGCACCTGTGTGGATC 3' (SEQ ID NO: 5); 5B2–5'GGGAATTCGTGACCATGGCAGT 3' (SEQ ID NO: 6)) were constructed on the basis of homologous domains of preproinsulin gene sequence of different fish species as mentioned in the text. The PCR was performed for 35 cycles of denaturation at 94° C. for 45 sec (5 mm in the first cycle), annealing at 50° C. for 45 sec and extension at 72° C. for 1 mm (10 min in the last cycle). As the enzyme recognizable sequences EcoRl and HindIII were tagged to the 5' termini of the sense primers and antisense primer oligo (dT) respectively, the RT-PCR products were digested by those enzymes. The digests were electrophoresed on 1.5% agarose gel; the band was excised and purified using QiaEx- II gel extraction kit. It was then cloned directionally into pBluescript plasmid vector (Stratagene) in EcoRl-HindIII site. Sequencing of the RT-PCR product was performed by Applied Biosystem Prism dye system automated sequencer. Amino acid and nucleic acid sequences of different organisms were collected from NCBI database.

Computational tools and hardware platforms for molecular modeling-predictions of 3-dimensional structures were done by knowledge-based homology modeling using InsightII 98.0 of MSI, ABGEN (22} and our in house package of MODELYN and ANALYN (23) in UNIX as well as m the MS Windows environment. Energy minimization and molecular dynamics were performed with the msightII 98.0/Discover package using cf(91 forcefield on a Silicon Graphics" OCTANE workstation. Energy minimizations were done with a convergence criterion of 0.001 kcal/mol, using a combination of steepest decent and conjugate gradient methods (100 steps each); these steps were repeated until satisfactory conformational parameters were obtained.

Molecular dynamics simulations were carried out using a time step of 1 fempto second for 100 steps of equilibration and 1000 steps of dynamics. Distance constraints were applied to the other parts of the molecule while running minimization and dynamics for regularization of selected segments. The electrostatic potential surfaces of the proteins were determined by MOLMOL (24). TREEVIEW software package, version 1.6.6 (25) was used for the construction of a phylogenetic tree, which read PHYLIP style treefiles produced by CLUSTALW (26) which was also used for multiple alignment of protein sequences. PROCHECK (27) was used for checking the structural parameters and comparing with reference protein structures.

Results

Figures 3A, 3B, 3C:
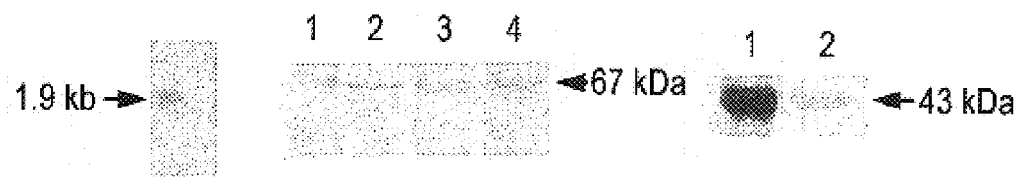
Figure 3D:
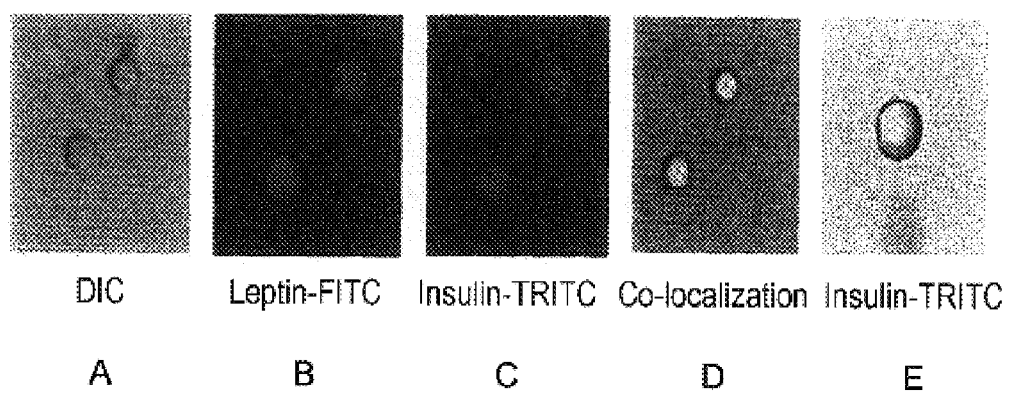

Immunoreactive and bioactive insulin from adipocytes—We were puzzled to find high amount of immunoreactive insulin (ir-insulin) in carp plasma without the existence of principle islet tissues. This led us to make a thorough search of different tissues for detecting the source of circulatory insulin. Surprisingly, adipocytes showed localization of ir insulin (FIG. 1), suggesting that these cells may secrete insulin. To examine this, we have isolated adipocytes, incubated them in vitro and then checked the medium for detecting ir-insulin. FIG. 2a shows that adipocytes can secrete considerable amount of ir-insulin while the medium of the hepatocytes and kidney cells did not show the presence of ir-insulin indicating specificity of this secretion. Bioactivity of this ir-insulin was examined by injecting the medium into the rat, which significantly reduced ($p<0.01$) plasma glucose level (FIG. 2b). Glucose is a known agonist of insulin secretion from pancreatic p-cell when concentration of glucose was increased to about 10 times in the incubation medium (MEM contained 5.5 mM glucose), insulin release was stimulated to more than 2-fold (FIG. 2c} suggesting glucose dependent insulin secretion. To confirm the identity of these cells as adipocytes, we examined following criteria—(i expression of adipocyte specific gene flotillin, (ii) presence of PPARy and (iii) presence of GLUT4. We have used mouse flotillin cDNA probe for Northern hybridization with RNA extracted from carp adipocyte. FIG. 3a shows hybridization signal with adipocyte RNA while RNA from carp muscle, liver and kidney did not produce any signal showing adipocyte specific hybridization. The hybridized transcript was –1.9 kb. Increasing amount of adipocyte extract produced greater cross-reaction with PPARy antibody (FIG. 3bl Although GLUT4 is not a specific marker of adipocytes, but its presence (FIG. 3c) distinguished them from pancreatic (3-cell which lacks GLUT4. Most striking evidence in flavour of adipocytes secretion of insulin was the co-localization of leptin and insulin by using immunofluorescence staining. Confocal microscopy (FIG. 3d) shows the localization of leptin and insulin in the same cell.

Figure 5A:
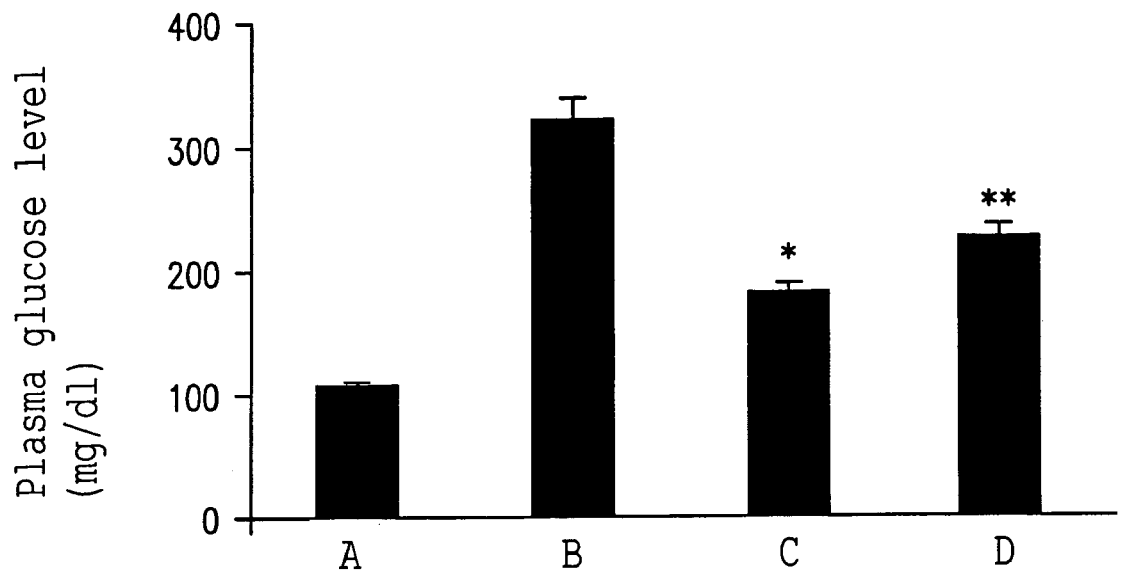
Figure 5B:
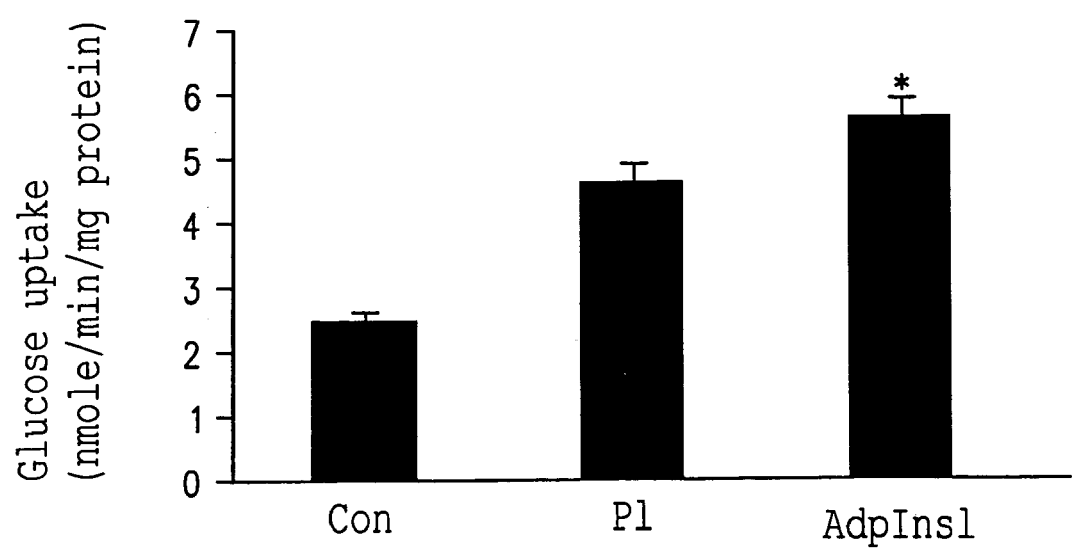

To purify insulin from the adipocyte, cells were lysed by sonication followed by solvent fractionation, gel permeation chromatography and FPLC reverse phase chromatography. Purified adipocyte insulin (AdpInsl) comigrated with porcine and bovine insulin in SDS-PAGE indicating closeness of their molecular size ~5.5 kDa (FIG. 4). Injection of AdpInsl to streptozotocin-induced diabetic rats significantly reduced hyperglycemia ($p<0.001$, as compared with control; its hypoglycemic activity was 25% greater than porcine insulin (FIG. 5a). AdpInsl stimulated more than 2-fold increase in glucose uptake by adipocyte, its stimulation was significantly higher ($p<0.05$) than porcine insulin (FIG. 5b).

Figure 6A:
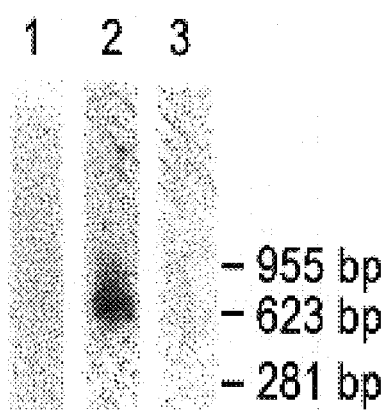
Figure 6B:
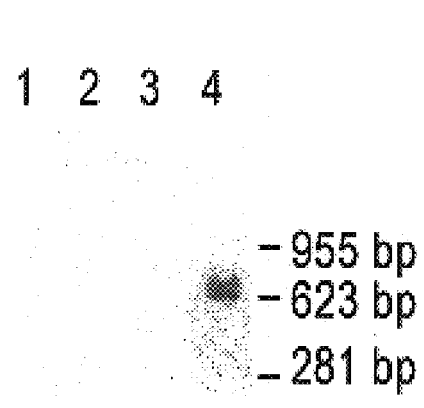

Insulin gene expression in adipocytes and cloning of AdpInsl—The most important question is whether adipocyte can express insulin gene. To resolve this, we have used insulin cDNA probe from rat and zebra fish for Northern hybridization with the RNA extracted from the adipocyte. FIG. 6a shows hybridization of adipocyte RNA with zebrafish and rat insulin cDNA while hybridization signal was not detected with the adipocyte RNAs from rat, guineapig and hamster (FIG. 6b). The size of the hybridized transcript was ~70Q bp which is close to pancreatic insulin gene.

To characterize AdpInsl gene, consensus oligonucleotide primer (SB-1) was designed from selected homologous domains of zebra fish (*Danio rerio*, GenBank Accession Number AF036326), European carp (*Cyprinus carpio*, GenBank Accession Number X00989), Salmon (*Onchorynchus keta*, GenBank Accession Number LI 1712) and Tilapia (*Tilapia nilotica*, GenBank Accession Number AF038123) preproinsulin cDNA. RT-PCR performed with adipocyte total RNA produced 375 bp DNA fragment using SB1 and oligo (dT) primers. This product was cloned and sequenced. Nucleotide sequence analysis of this clone showed more than 90% positional homology with preproinsulin gene of zebra fish. Amplified and sequenced portion of cDNA corresponded to AdpInsl A and C peptide regions but lacked 5'-sequences of cDNA corresponding to the B-chain. Since B chain of AdpInsl could not be sequenced with SB1 primer, another primer, SB2 was synthesized on the basis of Danio signal peptide sequence. This was expected to give us full sequence of B chain. Utilization of SB-2 and oligo (dT) primers in RT-PCR produced a 425 bp DNA fragment. The amplified DNA fragment was cloned and sequencing of this clone revealed complete AdpInsl signal peptide and complete 3' UTR (FIG. 7a, Gen Bank Accession Number AF373021(. Deduced amino acid residues of AdpInsl exhibited striking homology with pancreatic ft-cell insulin of different vertebrates (FIG. 7b). Its A and B chain showed 98% homology with zebra fish and more than 70% homology with human, pig and rat insulin, although there is very little homology at the nucleotide level.

Three-Dimensional Structural Modeling of AdpInsl and Insulin Receptor—We predicted the structure of the AdpInsl from the known structure of human insulin (17) based on the sequence alignment shown in FIG. 7b. Mutations were done on each of the 6 monomers containing A- and B-chains of the NMR derived structure followed by placement of the side-chains with minimum bumps with the surrounding atoms. The resulting hexameric structure was energy minimized and a monomer was separated to examine the effect of mutation and to map the electrostatic potential on its surface, as the monomer is the receptor-binding unit. Protein BLAST (28) search with the sequence of human insulin receptor (N-terminal LI-Cys-rich-L2 only) as a query sequence in the pdb database gave a single hit with 59% aa identities and 75% homologous match for the corresponding domains of the x-ray structure of IGF-IR (pdb ligr. ent). Therefore, the initial model of insulin receptor was built by taking that structure as the starting scaffold followed by mutation, insertion and deletion of amino acids based on the pair-wise sequence alignment as shown in FIG. 8. The structural regions, in which there insertions and deletions, were then regularized by repeated energy minimization and molecular dynamic simulations. The space-filling model is shown in FIG. 9A and superposition of the modeled structure of IR with the x-ray structure is shown in FIG. 9B. It may be noted that almost the whole of the structures superposed very well onto each other (Ca deviation about 0.08A) except for a major deviation in the cystine-rich domain (shown by arrow). Structures were checked by PROCHECK (27) in order to validate the structural parameters Comparison between AdpInsl and human insulin in reference to receptor binding—alanine scanning mutagenesis of insulin showed that receptor binding is very strongly affected by mutations at Gly-B23 and Phe-B24 of B chain and Ile-A2, Val-A3 and Tyr-A19 of the A chain. These amino acids (FIG. 7, red) have been colored red in the structures of both the fish (FIG. 10A) and human (FIG. 10B) insulin. Some other amino acids that are known to affect the receptor binding to some extent (FIG. 7, pink) have been colored pink in both these structures. These structures are then oriented in such a way that the receptor binding regions are placed at the front (inside the yellow ring, FIGS. 10A&B). It is noteworthy that although the fish insulin differ with its human counterpart in a number of aa in both the chains (FIG. 7) the strategically important amino acids provide strikingly similar structural motif differing by only one aa i.e. at the $8^{th}$ position of the A chain (His in fish and Thr in human, FIG. 7).

Side-chain of the His-A8 residue, points along the surface of the helix making the N-terminal a-helix more stable which was also demonstrated by NMR studies on an engineered variant of human insulin and this change favored receptor binding by 43% (6). FIG. 10C (AdpInsl) and 10D (human insulin) show the electrostatic potential at these surfaces, which are most probably the complementary regions in the ligand-receptor interface. The central parts of these surfaces in both the AdpInsl and human insulin are neutral indicating the dominance of hydrophobic forces in receptor binding. There is a slight difference at the upper right corner of the yellow ring where the fish insulin is basic (FIG. 10C) but the human insulin is acidic (FIG. 10D) in nature.

Strategically important sites on the receptor surface for insulin-binding—FIG. 9C shows the strategically important residues on the surface of the insulin receptor (within the yellow ring). The residues (Arg-14, Asn-15 and Phe-64, colored in red), when mutated (to Ala) causes about 300 fold reduction in the ligand-binding affinity, whereas mutations in residues (Ile-13, Gin-34, Leu-36 and Phe-39, colored in pink) cause 10–100 fold reduction and mutations in the residues (Asp-12, Met-38, Glu-44, Tyr-66, Phe-89, Asn-90 and Tyr-91, colored in light blue) cause 3–9 fold reduction in the binding affinity. This patch on the LI domain is expected to play an important role in the ligand binding on insulin receptor. The electrostatic potential on the corresponding area is shown in FIG. 9D. It may be pointed out that this region is electrostatically a mixture of neural (white patches) and positively charged (blue patches) residues. However, ligand binding to the insulin receptor is much more complicated as evidenced from the in vitro studies with monomeric and hybrid receptors, so the identified area represents only a potential binding zone.

In another embodiment of the present invention, wherein the SEQ ID No.1 refers to Insulin chain A as shown in FIG. 7(b). Also, SEQ ID No. 2 refers to chain B of the Insulin as shown in FIG. 7(b). Further, SEQ ID No. 3 refers to Insulin gene of FIG. 7(a). In addition, SEQ ID Nos. 5 and 6 refer to primers SB 1 and SB2 respectively.

Discussion

We have serendipitously discovered carp adipocyte as an exceptional cell where insulin gene is expressed and protein is secreted. To prove adipocyte identity we have used adipocyte specific expression of flotillin gene; leptin and PPARy protein as markers. Co-localization of insulin and leptin strengthens the special attributions displayed by these cells. Although presence of insulin has been shown in certain invertebrates (2) and in the extrapancreatic tissues of rat and human (3) but expression of insulin gene and secretion of insulin is still known to be pancreatic p-cell specific. Our investigation shows that novel insulin AdpInsl from carp adipocyte is structurally and functionally very similar to pancreatic p-cell insulin. Like pancreatic P-cell insulin AdpInsl is composed of two polypeptide chains, an A chain of 21 amino acid residues and a B-chain of 30 amino acid residues. AdpInsl has 98% homology with zebrafish p-cell insulin and more than 70% homology with porcine and human insulin. Although there is a considerable homology in the sequence of amino acid between AdpInsl and mammalian insulin, at the nucleotide level it is not so as different codons have been used for the same amino acids. About 85% nucleotides in AdpInsl and zebrafish are different from mammalian insulin indicating a change of genetic make up in the evolution of insulin molecule keeping peptide structure more conserved. If we consider the peptide segments of insulin involved in transducing signals by recognizing the surface receptor molecule, they remain far more conserved as compared to two peptide chains. AdpInsl originates from carp adipocyte, which is a lower vertebrate and even there the critical determinant segment for receptor binding is highly homologous to mammalian insulin. Probably to retain its similar biological activity throughout the vertebrate series such conservation of receptor recognition domain exists. It is difficult to interpret why such a change in genetic make up occurred in the evolution of insulin keeping peptide structure more conserved.

Functionally AdpInsl is more active than porcine insulin in rat. Injection of AdpInsl into the streptozotocin induced diabetic rat produced significantly stronger hypoglycemic effect as compared to porcine insulin. AdpInsl stimulated glucose uptake by adipocyte more actively than porcine insulin. All these indicate a better recognition of insulin receptor (IR) by AdpInsl. This prompted us to compare peptide segment of AdpInsl with porcine and human insulin in relation to receptor interactions. A1–A8 sequence (GIVEQCCT) (SEQ ID No: 16) of porcine and human insulin contains critical determinants of receptor binding. The importance of this segment in IR interactions was recognized early by measuring the biological activity for various derivatives (29,30). The A1–A8 sequence has low intrinsic helical propensities and an unfavorable C-cap residue (Thr$^8$) (31). Substitution between A1–A3 aa residues is detrimental to biological activity (32–35). On the other hand substitution of His or Arg for exhibits significant increase in activity (36) in accordance thermodynamic stabilization with an enhancement of the folding stability (6,37). AdpInsl has His$^8$, a favorable substitute against unfavorable Thr$^8$ in human insulin and that explains the reason for its greater biological activity. Moreover, the most important segment of insulin peptide related to the receptor binding includes A1–A4, A19, B12 and B24–B26 (6) and AdpInsl has all these segments in position.

The predicted model of AdpInsl exhibited good structural parameters; in the Ramachandran's plot of φ-ψ dihedral angles only one (Gln-B4) aa is in the disallowed region compared to three (Gln-B4, Cys-137 and Ile-A10) in the NMR structure. The root mean square deviation (RMSD) of bond lengths and bond angles are 0.0301 A and 3.42° respectively in the modeled structure compared to 0.0295A and 3.24° in the reference-NMR structure (24). In case of the receptor model most of the <Ι>—if dihedrals fall in the core area (72.5% compared to the 78.4% in the x-ray structure). RMSD of bond lengths and bond angles in the modeled structure are 0.028Å and 3.69° respectively compared to 0.024Å and 3.12° in the reference x-ray structure (22). In absence of any experimentally determined structures these models are very helpful in the analysis of the structural features involved in the interaction of AdpInsl with the insulin receptor.

Insulin and insulin-like growth factors are well-studied molecules in terms of both biochemical and structural aspects. Important amino acids in relation to receptor binding activity have been mapped onto the surface of the insulin structure through a series of single and multiple mutations (12), analysis of natural variants and design of non-standard insulin (35). Mutations over millions of years of evolution have changed the sequence of insulin by keeping its main functionalities unaffected, thus maintaining the structural complementarities with its receptor. It is an interesting observation that there is about 29% (15 out of 51) difference in the amino acids of A and B chains of AdpInsl and human insulin but the biological function of this key molecular switch is well conserved (FIG. 7). Structural comparison between human insulin and AdpInsl reveals that there is a small difference among key residues involved in the interaction with the; receptor (only one aa at $8^{th}$ position of A chain), which provides almost the same surface complementarity (FIGS. 10A & B). It may be pointed out that the only difference in this structurally important region is the replacement of threonine at the A8 of human is with a histidine residue in AdpInsl. It has been demonstrated that the same mutation in an engineered insulin resulted in 43% increase in its receptor binding affinity compared to human insulin (6). High-resolution NMR studies established that there is a significant increase in the helical character of the N-terminus of the A-chain (aa A2 to AS) due to this replacement. This structural change leads to additional exposure of a hydrophobic patch mainly consisting of species invariant residues known to be critical for receptor interactions (6). His-A8 also serves as a favorable C-cap residue in the N-terminal a-helix making it thermodynamically more stable compared to the Thr-A8 of human insulin (35). Thus the adipocyte insulin, as histidine occurs naturally at its A8 position, is expected to have higher affinity for insulin receptor than the human or porcine insulin. From our experimental observation it is evident that this adipocyte insulin acts on the rat receptor (which is 96% identical with human, 100% identical in the potential binding region) with the higher efficiency than the porcine insulin.

In vitro insulin binding to detergent-solubilized whole $(\alpha\beta)^2$ human insulin receptor induces large conformational changes resulting in the change of Stokes radius from 9.1 to 7.5 nm and the sedimentation coefficient from 10. IS to 11.4 S (38) Binding of insulin to the whole receptor also exhibits curvilinear Scatchard plots and negative cooperativity indicating more than one binding sites. On the other hand, insulin binding to αβhalf receptor or IR/IGF-1R hybrid receptors is very different in nature indicating the importance of the $(\alpha\beta)^2$ native state of the dimer (39). Probably the native dimer in the membrane embedded state is the most relevant conformation to simulate the in vivo conditions. However, precise determination of the insulin binding site on the receptor surface and the elucidation of the mode of interaction would require the experimental determination of the 3-D structure of the complex between insulin and its receptor.

Physico-chemical studies on 'the complexes between insulin and detergent solubilized whole $(\alpha\beta)^2$ receptor, ap half receptor or IR/IGF-1R hybrid receptors indicate that there are more than one binding site with varying affinites (38,39). Therefore, the surface indentified on the modeled human insulin receptor (FIG. 9C) represents one of the probable binding sites of insulin. However, precise determination of the insulin binding site on the receptor surface and the elucidation of the mode of interaction would require the experimental determination of the 3-D 17 structure of the complex between insulin and its receptor, information on which is still not available. Our study on AdpInsl has opened an area of considerable interest where insulin from a nonconvetional cell exhibited greater functionality coinciding with favored structural attributions. The main advantages of the present invention are:

1. It affords carp adipocyte as an exceptional cell where insulin gene is expressed and protein secreted.
2. Functionally AdpInsl is more active than procine insulin in rat.
3. AdpInsl stimulated glucose uptake by adipocyte is more active than procine insulin.
4. AdpInsl acts on the rat receptor which is 96% identical with that of human, 100% identical in the potential binding region, with higher efficiency than porcine insulin.

REFERENCES

1. Le Roith, D., Shiloach, J., Heffron, R., Rubinovitz, C., Tanenbaum, R., and Roth, J. (1985) *Can J. Biochem. Cell Biol.* 63(8), 839–849
2. Le Roith, D., Lesnaik, M. A., and Roth, J. (1981) *Diabetes* 30(1), 70–76
3. Rosenzweig, J. L., Havrankova, J., Lesniak, M. A., Brownstein, M., and Roth, J. (1980) *Proc. Natl. Acad. Set. U.S.A.* 77(1), 572–576
4. Plisetskaya E. M. (1989) *FishPhysiol. Biochem.* 7, 39–48
5. Cosmatos, A., Cheng, K., Okada, Y., and Katsoyannis, P. G. (1978) *J. Biol. Chem.* 253, 6586–6590
6. Olsen, H. B., Ludvigsen, S., and Kaarsholm, N. C. (1998) *J. Mol. Biol.* 284, 477–488
7. Pullen, R. A., Lindsay, D. Q., Wood, S. P., Tickle, I. J., Blundell, T. L., and Wollmer, A. (1976) *Nature* 259, 369–373
8. Hua, Q. X., Shoelson, S, E., Kochoyan, M., and Weiss, M. A. (1991) *Nature* 354, 238–241
9. Ludvigsen, S., Olsen, H. B., and Kaarsholm, N. C. (1998) *J. Mol. BioL* 279, 1–7
10. DC Meyts, P. (1994) *Diabetologia* 37, 135–148
11. Chakrabartty, A., Kortemme, T., and Baldwin, R. L. (1994) *Protein ScL* 3, 843–852
12. Kristensen, C., Kjeldsen, T., Wiberg, F. C., Schaffer, L. H S. (1997) *J. Biol Chem.* 272, 12978–12983
13. Conlon, J. M. (2001) *Ptptides* 22, 1183–1193
14. McDonald, N. Q., Murray-Rust, J., and Blundell, T. L. (1995) Structured, 1–6
15. Garrett, T. P. J., McKern, N. M., Lou, M. Z., Frenkel, M. J., Bentley, J. D., and Lovrcci Q. O. (1998) *Nature* 394, 395–399
16. T. E., Epa, V. C., Garrett, T. P. J., and Ward, C. W. (2000) *Cell Mol Life Sd.* 57, 1050–1093
17. O'Donoghue, S. I., Chang, X., Abseher, R., Nilges, M., and Led, J. J: (2000) *J. Biomol NMR* 16, 93–108
18. Sambrook, J., Fritsch, E. F., and Maniatis, T. (1989) Moleculart Cloning: A Lab. Manual. $2^{nd}$ Edition, Cold Spring Harbor Laboratory, Cold Spring Harbor, N.Y.

19. Lowry, O. H., Rosebrough, N*.J., Farr, A. E., and Randali, R. J. (1951) *J. Biol Chem.* 193, 265-^&5
20. Lacmmli, U.K. (1970) *Nature* 27, 680–685 v
21. Marshall S., Bacote, V., and Traxinget R. R. (1991) *J. Biol. Chem* 266, 4706–4712
22. Mandal, C., Kingery, B. D., Anchin, J. M., Subramanium, S., antt Linthicum. D.S. (1996) *Nature (Biotechnology)* 14, 323–328
23. Mandal, C. (1998) MODELYN—A molecular modelling program version PC-1.0 Indian Copyright No 9/98
24. Koradi, R., Billeter, M., and Wuthrich, K. (1996) *J. Mol. Graph.* 14, 29–32, 51–55
25. Page, R. D. M. (1966) *Computer Applications in the Biosciences* 12, 357–358
26. Thompson, J. D., Higgins, D. G., and Gibson. T. J. (1994) *Nucleic Acids Res.* 22, 4673–4680
27. Laskowski, R. A., MacArthur, M. W., Moss, D. S., and Thornton, J. M. (1993) *J. Appl. Cryst.* 26, 283–291
28. Altschul, S. F., Madden, T. L., Schaffer, A. A., Zhang, J., Zhang, Z., Miller, W. and Lipman, D. J. (1997) *Nucleic Acids Res.* 25, 3389–3402
29. Geiger, R., Geisen, K., Reqitz, G., Summ, H. -D., and Langner, D. (1980) *Hoppe-Seyler's Z. Physiol. Chem.* 361, 563–570
30. Geiger, R., Geisen, K., and Summ, H. -D. (1982) *Hoppe-Seyler's Z. Physiol. Chem.* 363, 1231–1239
31. Baker, E. N., Blundell, T. L., Cutfield, J. F., Cutfiled, S. M., Dodson, E. J., Dodson, G. G. et al. (1988) *Phil. Trans. Roy. Soc. London.* 319, 369–456
32. Kitagawa, K., Ogawa, H., Burke, G. T., Chanley, J. D., and Katsoyannis, P. G. (1984) *Biochemistry* 23, 1405–1413
33. Kobayashi, M., Takata, Y., Ishibashi, O., Sasaoka, T., Iwasaki, T. M., Shigeta, Y., and Inouye, K. (1986) *Biochem. Biophys. Res. Commun.* 137, 250–257
34. Nakagawa, S. H., and Tager, H. S.$_y$ (1992) *Biochemistry* 31, 3204–3214
35. Weiss, M. A., Wan, Z., Zhao, M., Chu, Y. -C., Nakagawa, S. H., Burke, G. T., Jia, W., Hellmich, R., and Katsoyannis, P. G. (2002) *J. Mol. Bio/.* 315, 103–111
36. Marki, F., Gasparo, M. D$_M$ Eisler, K., Kamber, B., Riniker, B., Rittel, W., and Sieber, P. (1979) *Hoppe-Seyler's Z. Physiol Chem.* 360, 1619–1632
37. Kaarsholm, N. C., Norris, K., Jorgensen, R. J., Mikkelsen, J., Ludvigsen, O. H. et al. (1993) *Biochemistry* 32, 10773–10778.
38. Florke, R -R., Klein, H. W., and Rejnauer H. (1990) *Bur. J. Biochem.* 191, 473–482
39. Siddle, K., Urso, B., Niesler, C. A., Cope, D. L., Molina, L., Surinya, K. H., and Soos, M. A. (2001) *Biochem. Soc. Trans.* 29(Pt 4), SIS-525.

The invention claimed is:

1. An isolated adipocyte Insulin consisting of an A chain comprising SEQ ID NO: 1 and a B chain comprising SEQ ID NO: 2.

2. An Insulin as claimed in claim 1, wherein the SEQ ID No. 1 is of length 21 amino acids.

3. An Insulin as claimed in claim 1, wherein the SEQ ID No. 2 is of length 30 amino acids.

4. An insulin as claimed in claim 1, wherein the insulin shows amino acid residue Histidine at position eight of Insulin A chain.

5. An insulin as claimed in claim 1, wherein the insulin shows 70% homology with human insulin.

6. An insulin as claimed in claim 1, wherein the insulin shows segments A1–A4, A19, B12, and B24–B26 as receptor binding segments.

7. An insulin as claimed in claim 1, wherein the binding regions of insulin is 100% identical to the corresponding regions of human insulin.

8. A method of treating type 2 diabetes in a subject using adipocyte insulin, said method comprising steps of administering an effective amount of adipocyte insulin to a diabetic intraperitoneally.

9. A method as claimed in claim 8, wherein the insulin is of concentration ranging between 15 to 20 micrograms per 100 grams body weight.

10. An insolated nucleic acid comprising of SEQ ID No. 3.

11. A process of isolating protein Insulin from the adipocytes of the Carp, said method comprising steps of:
   a. reverse transcripting RNA of adipocytes to obtain cDNA,
   b. using oligonucleotide primers of SEQ ID Nos. 5 and 6 to identify AdpInsl gene from cDNA,
   c. deducing amino acid sequence from cDNA to obtain protein Insulin.

12. A process as claimed in claim 11, wherein the primer of SEQ ID No. 5 along with oligo (dT) primer produces DNA fragment of 375 bp.

13. A process as claimed in claim 11, wherein the primer of SEQ ID No. 6 along with oligo (dT) primer produces DNA fragment of 425 bp.

* * * * *